United States Patent [19]

Laerum

[11] Patent Number: 5,695,518
[45] Date of Patent: Dec. 9, 1997

[54] FILTERING DEVICE FOR PREVENTING EMBOLISM AND/OR DISTENSION OF BLOOD VESSEL WALLS

[76] Inventor: Frode Laerum, Ovre Ullern, Terasse 17, NO-0380 Oslo 3, Norway

[21] Appl. No.: 418,618

[22] Filed: Apr. 7, 1995

Related U.S. Application Data

[63] Continuation-in-part of Ser. No. 78,317, filed as PCT/FR91/01076, Dec. 27, 1991, abandoned.

[30] Foreign Application Priority Data

Dec. 28, 1990 [FR] France ................... 90 16516
Dec. 27, 1991 [WO] WIPO .............. PCT/FR91/01076

[51] Int. Cl.$^6$ ................ A61B 17/00; A61F 2/02; A61M 25/00
[52] U.S. Cl. ............ 606/200; 606/195; 606/198; 604/60
[58] Field of Search ............... 606/195, 198, 606/200; 604/57, 59, 860; 128/899; 623/1, 12; 267/156, 272; 368/140

[56] References Cited

U.S. PATENT DOCUMENTS

| | | | |
|---|---|---|---|
| 1,710,576 | 4/1929 | Guett | 267/156 |
| 3,590,816 | 7/1971 | Rose | 604/60 |
| 4,553,545 | 11/1985 | Maass et al. | 606/198 |
| 4,834,725 | 5/1989 | Iwatschenko | 604/281 |
| 4,957,501 | 9/1990 | Lahille et al. | 606/200 |
| 4,994,069 | 2/1991 | Ritchart et al. | 606/200 |
| 5,217,484 | 6/1993 | Marks | 606/200 |

FOREIGN PATENT DOCUMENTS

| | | |
|---|---|---|
| 0 201 466 | 11/1986 | European Pat. Off. . |
| 2 541 901 | 9/1984 | France . |
| 2 645 731 | 10/1990 | France . |
| 32 03 410 | 11/1982 | Germany . |

OTHER PUBLICATIONS

Laerum et al., "In Vitro Function of the Temporary Venous Spring-Filter Compared to Filcard Temporary Filter and Greenfield Vena Cava Filter", Feb. 24, 1995.
Laerum et al., "In Vitro Assessment of the New Adjustable Temporary Venous Spring-Filter", Feb. 26, 1995.
The Wm. D. Gibson Company, *Catalogue No. 9, Springs,* Chicago, IL, 1923, pp. 30–31.
Barnes-Gibson-Raymond, Division of Associated Spring Corporation, *Mechanical Springs, Their Engineering Design,* Detroit, MI, 1948, pp. 82–84.
Chironis, *Spring Design and Application,* McGraw-Hill Book Co., Inc., 1961, pp. 36–37.

*Primary Examiner*—Michael Buiz
*Assistant Examiner*—Nancy Mulcare
*Attorney, Agent, or Firm*—Foley & Lardner

[57] ABSTRACT

A filtering device and method of preventing embolism and/or the distension of blood vessel walls is provided. The device can be easily put in place and can also be removed from the patient. The device comprises a spring-like active part and a rectilinear actuator. The actuator is used to prolongate or activate the active part. The active part has a shape memory corresponding to the shape of a spiral or a semi-circle. The active part can be straightened and will regain its shape memory position upon installation in the patient's vein. The filter can be used on blood vessels of various sizes because the user can vary the amount of the active part regains its original configuration in the vein. The filter can be secured into place and has the advantage of being removable when no longer needed.

11 Claims, 6 Drawing Sheets

FILTERING DEVICE FOR PREVENTING EMBOLISM AND/OR DISTENSION OF BLOOD VESSEL WALLS

This application is a continuation-in-part of U.S. Ser. No. 08/078,317, filed as PCT/FR91/01076, Dec. 27, 1991, now abandoned.

BACKGROUND OF THE INVENTION

The present invention is related to a filtering device for the prevention of embolism and/or the distension of the blood vessel walls.

It is known that embolisms are the result of the obliteration of a blood vessel by a foreign body, such as a blood clot, which is conveyed by the blood to the point where the diameter will not be sufficient to permit its passage. Thus, pulmonary embolisms are generally provoked by the emboli, which originate from thrombosis or phlebitis of the lower limb, travelling from this location in the direction of the pulmonary artery via the inferior vena cava and the right-hand cardiac circulation.

Pulmonary embolism is a common complication in patients confined to bed, in particular in the post-operative period or in the elderly during recovery of inflammatory or stroke diseases. It may also be problematic in the young patient after trauma or delivery.

Pulmonary embolism is the most common direct cause of death during the terminal period of life. The embolus is most commonly provoked by a deep venous thrombosis (DVT) of the lower limb. Survivors of a lung embolus may encounter profound damage to the lung vasculature and chronic pulmonary hypertension leading to death.

Deep venous thrombosis is observed in up to 60% of the patients after hip surgery, but is also frequent after other surgical procedures. It is thus in this way that deep venous thrombosis is a significant clinical problem in stroke diseases, after myocardial infarction, in certain forms of cancer or in patients with altered blood coagulation.

The treatment of deep venous thrombosis is dominated today by systemic medication with heparin or heparin fragmin, in addition to anticoagulation treatment with cumarin.

In younger patients and in severe, selected cases (i.e. pelvic vein thrombosis), also systemic fibrinolytic treatment may be used. However, systemic treatment is not without complications, particularly hemorrhages.

In recent years local treatment has been pursued, like surgical thrombus removal from the pelvic vein combined with artificial arteriovenous fistula in the groin and anticoagulant medication. The results are varying, but this treatment has not been adopted on a broad base.

A deep venous thrombosis finds its natural development towards lysis, or results in obstruction of the veins or in the destruction of the valves. Such post-thrombotic states lead in their turn to venous insufficiency, enhanced venous pressure peripherally, the formation of anastomosis and varices. The end effect may be of great nuisance to the patients and forms a significant socio-economic problem.

Further, mechanical filters have been employed in the inferior caval vein in patients with deep venous thrombosis to prevent the embolus from migrating to the pulmonary arteries.

Such filters are generally loaded in the vein temporarily or permanently, in an upper (jugular) or lower (femoral) percutaneous way by means of catheters or in a surgical manner (plication).

Today, the most employed mechanical filter is the Greenfield filter, which comprises a plurality of undulated wires, which are distributed along a cone from a common vertex.

Other filters, such as the Mobin-Uddin filter, the Giant-urco filter, the Amplatz filter, the Günther basket filter are also used.

Although some of these known filters are formed to permit retrieval, their removal is generally very complicated in practice. They may also dislodge, penetrate into the venous wall or cause local thrombotic reactions followed by obstruction of the caval vein.

Further, the dissection of the wall tunicae may cause the forming of false channels obstructing the branching arteries. This is a rare, but life-threatening disease with a sudden onset.

There is also a filtering device, known in particular through the documents FR-2 625 437 and FR-2 632 864 of Société BIOMAT and FR-2 541 901 of Monsieur Franceschi, comprising an active part intended to be placed in the blood flow and in the form of a wire in a shape memory material, which can be brought into a substantially rectilinear position and which will regain its initial deformation when it is released, in which it causes a deformation of the vessel without stopping the flow, thereby permitting the stopping of the migration of large blood clots coming from the peripheral venous network.

In the employment position, these devices are either in the form of two ellipses, the major axes of which form an angle of 90° between themselves (FR-2 625 437 and FR-2 632 864), or in the form of primary and secondary undulations extending in separate planes (FR-2 541 901).

It is however, difficult to remove such devices, and they are not adapted for a temporary loading in the vessels.

SUMMARY OF THE INVENTION

The present invention thus aims at solving the new technical problem of providing a filtering device of a new kind intended to prevent emboli and/or distension of the blood vessel walls, which permits temporary or permanent loading.

According to the present invention, the solution to this technical problem comprises a filtering device for the prevention of embolism and/or the distension of the blood vessel walls of the type comprising an active part intended to be placed in the blood flow and in the form of a wire in a shape memory material, which can be brought into a substantially rectilinear position and which will regain its initial deformation when it is released, characterized in that said wire, in its state of initial deformation, has the form of a flat spiral spring or a semi-circular curve.

This solution permits the solving of the above-mentioned problem in an extremely simple manner, which is easy to employ on the industrial base.

According to a particular characteristic feature of the filtering device of the invention the active part is prolongated at its end by a semi-flexible wire, which is intended to introduce, retrieve and to secure the active part in operating position in the blood vessel.

According to the first embodiment, the semi-flexible wire extends in the same plane as the active part.

This configuration is particularly advantageous in that a filter of a single size may be used for vessels of variable sizes. In fact, as the active part is formed in the shape of a spiral spring, it will of course be possible, in the case of a small-size vein, to introduce only a portion of this spiral in the vessel, or, in the case of a vein of a larger size, a larger portion of this spiral.

Thus, this filter is suitable for a large number of venous diameters and its operation may be optimized in a more individualized manner thanks to a better hemodynamic adjustment at the filter site.

According to another embodiment of the invention, the semi-rigid wire extends in a plane which is substantially perpendicular to the plane of the active part.

This embodiment is particularly useful to temporarily compress the tunicae in order to prevent the continuation of the dissection or to compress the entrance to the false channels. In this way, it is also possible to use the spiral device as a more conventional filter in the caval vein.

According to a further embodiment of the invention the shape memory wire is provided between two catheters. Relative movement of the catheters allow the wire to regain its initial deformation of a semi-circle.

This arrangement provides the advantageous feature of providing a filter device which operates in one plane and with minimal tilting in the axial plane.

BRIEF DESCRIPTION OF THE DRAWINGS

The invention will be more clearly understood, and other scopes, characteristic features and advantages thereof will appear more clearly after reading of the following explanatory description, which is made with reference to the diagrammatic drawings, which are presented only as non-limitative examples, and illustrating presently preferred embodiments of the invention, in which.

DETAILED DESCRIPTION OF THE PREFERRED EMBODIMENTS

Referring initially to FIGS. 1a, 1b, 2a, 2i b, a filtering device (hereinafter "filter") of the present invention essentially comprises an "active" part 1, which is prolongated at its end by a substantially rectilinear member, flexible wire 2, which is intended to introduce, retrieve and to secure said active part in position in a blood vessel.

The active part 1, which is intended to be placed in the blood flow, is in the form of a wire of a shape memory material, which can be brought into a substantially rectilinear position to be loaded into a catheter and which will regain a shape corresponding to its initial deformation when it is released in the vessel.

Figure 1A:
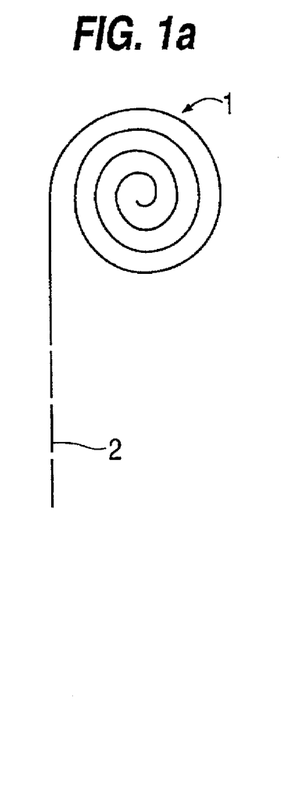
FIG. 1a is a diagrammatic front view of a filtering device according to a first embodiment of the invention.

The shape memory material used may be metallic or plastic. Preferably, the wire used has a diameter between 0.2 and 2 mm. It is manufactured, for instance, in stainless steel of medical quality and has a diameter of between 0.2 and 1 mm. It may also be manufactured in a plastic material with a diameter of between 0.2 mm and 2 mm or in stainless steel (0.05 to 1 mm) coated with a plastic material with a diameter of 0.2 to 1.5 mm. Moreover, the shape memory material may have a decreasing (taped) diameter from the outer end of the active part 1 toward the rectilinear member 2.

Figure 1B:
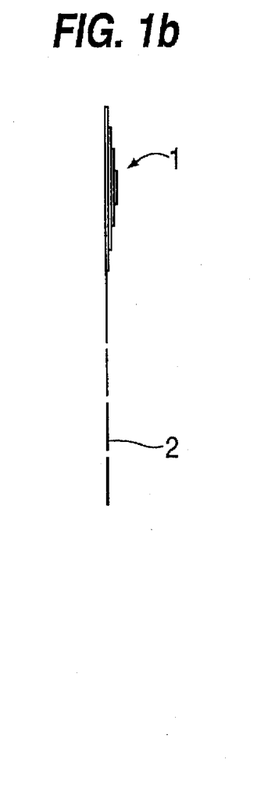
FIG. 1b is a side view thereof.

As FIGS. 1a and 1b show, the wire, which constitutes the active part, has the form of flat spiral spring (clock spring) in its state of initial deformation. This wire can be brought into a substantially rectilinear position, in which it may be loaded into the catheter, which serves to load the filter. As it is manufactured in a shape memory material, it will regain its initial shape (clock spring) as soon as it has left the introduction catheter after its loading in the blood vessel.

The flexible wire 2 may be manufactured in the same material as the wire which constitutes the active part 1, however, the flexible wire 2 does not have a memory shape, and is thus a nonshape-memory portion. It may also be manufactured in a heterogenous material.

The wire 2, which prolongates the active part 1, may extend in the same plane as the active part 1 (i.e. in the plane of the clock spring) as FIGS. 1a and 1b show.

Figure 2A:
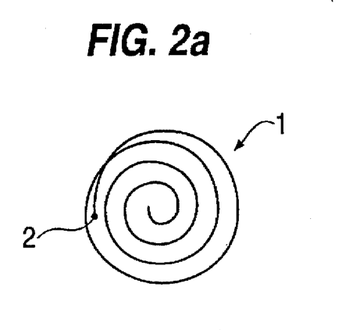
FIG. 2a is a diagrammatic front view of a filtering device according to a second embodiment of the invention.
Figure 2B:
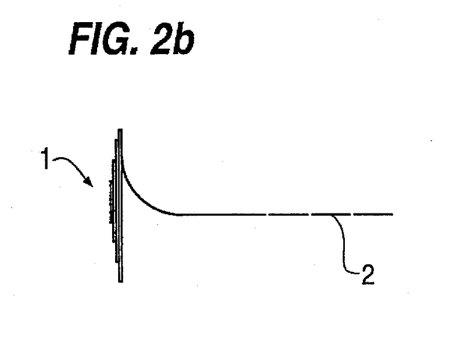
FIG. 2b is a side view thereof.

According to an embodiment, the wire semi-flexible 2 may be disposed substantially perpendicular to the plane of the active part, as shown in FIGS. 2a and 2b.

According to the invention, the loading of a filtering device inside a blood vessel may be effected in a manner, which is know per se, by pushing by means of the semi-flexible wire 2 through an introduction sheath, which has been positioned in advance in the vessel, in which the device is to be placed.

The equipment, which is generally needed for the loading, thus comprises an introduction sheath or catheter, the inner diameter of which will be generally of about 3 mm.

There will also be provided securing means for the filtering device, such as, for instance, a safety pin or another fastening device secured at a distal site.

The filtering device illustrated in FIGS. 1a and 1b fits a substantial number of venous calibers.

Figure 3A:
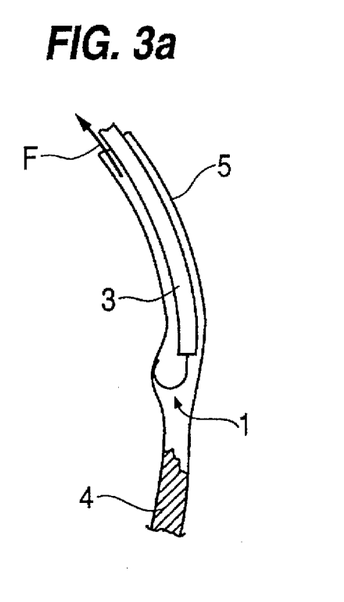
FIG. 3a is a diagrammatic, longitudinal section illustrating the loading of a filtering device of the type shown in FIG. 1a and 1b, inside a small-size vein.

Thus, as will be understood with reference to FIG. 3a, in the case of a small-size vessel 5, such as a small vein, only a small portion of the active part will be pushed passed the introduction catheter 3, after which a safety pin or another securing device and the introduction catheter are attached to one another and the system is secured at the distal introduction site (outside the vein). The filtering device will of course be placed above the venous thrombosis 4 in a centered manner (the blood flowing being indicated by the arrow F).

Figure 3B:
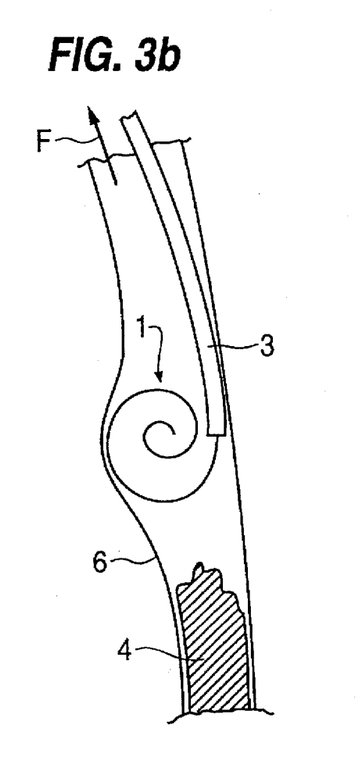
FIG. 3b is a view, which is similar to FIG. 3a, illustrating the loading of a filtering device of the same type inside a vein of a larger size.

In the case of a larger sized blood vessel 6 (FIG. 3b), a larger portion of the active part 1 will be fed, thus enlarging the total diameter, before locking the system to obtain the desired hemodynamic effects at the site of the filtering device.

In its modified version (FIGS. 2a and 2b), the filtering device of the invention is employable for the distension of the dissecting arterial walls or as a vena cava filter catching the emboli.

Figure 3C:
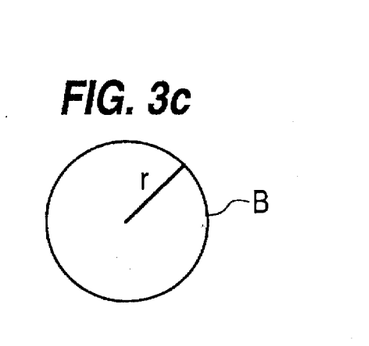
FIG. 3c is a cross-sectional view of a vein without the filtering device.
Figure 3D:
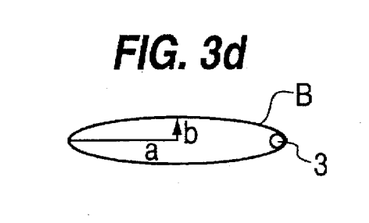
FIG. 3d is a cross-sectional view of a vein with the filtering device of the type shown in FIGS. 1a and 1b.
Figure 3E:
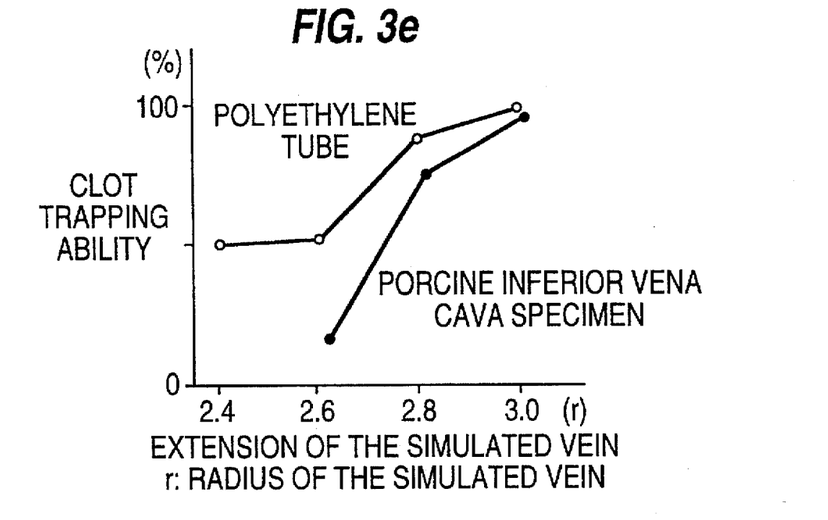
FIG. 3e is a graph showing the results of in vitro test of the filtering device. The graph shows the relationship of the clot trapping ability of the filtering device in relation to the degree the vein is extended.

Therefore, when the active part 1 is placed into the blood vessel and regains its original memory shape, the blood vessel B will be deformed from its original circular cross-sectional shape as shown in FIG. 3d into an ellipse as shown in FIG. 3e.

In order to achieve the most effective use of the filtering device the diameter of the initial shape (clock spring) of the active part 1 should be selected to cause a maximum possible deformation of the blood vessels B. The diameter of the initial shape (clock spring) that will be most effective is determined using the geometry of the blood vessel before and after insertion of the active part 1. This diameter is called the effective coil diameter.

Specifically, as shown in FIG. 3d, the blood vessel B has a circular cross-section with a radius r prior to insertion of the filter device. The radius r of the blood vessel B can be determined using standard practices, such as ultrasound. After the filtering device has been inserted into the blood vessel B and the active part 1 regains its initial shape, the cross section of the blood vessel B forms an ellipse. As shown in FIG. 3d, the ellipse has a long radius a and a short radius b. To insure that the blood vessel B forms an ellipse when the active part 1 regains its initial shape, the effective coil diameter must be greater than twice the radius r of the blood vessel B shown in FIG. 3c. The maximum effective coil diameter is determined by the distendability of the blood vessel B. Accordingly, in a preferred embodiment of the invention, the effective coil diameter will be between 12–35 mm, whereby the coils of the active part 1 shown in FIG. 1 will be 3–5 mm apart. More particularly, the spacing between the coils of the active part 1, in the preferred embodiment, will be 4 mm apart.

Furthermore, in vitro clinical testing has demonstrated that the clot trapping ability of the filtering device depends on the degree the blood vessel B, i.e. the vein, is deformed by the active part 1. FIG. 3e shows a chart comparing the clot trapping ability of the filtering device with the radius of a simulated vein. In testing, a polyethylene tube and a porcine inferior vena cava specimen were used as the simulated veins. As shown by the graph when the simulated vein is extended by the filtering device to a diameter that is greater than three times the radius of the blood vessel, over 90% of the clots are trapped by the filtering device. Accordingly, as shown in FIG. 3d, as the short radius b, shown in FIG. 3d, approaches zero, and the long radius a approaches three times the original blood vessel B radius r, the clot trapping ability of the filter device improves. During testing, clots of 6×10, 6×20, and 9×20 mm were used in the simulated veins.

Figure 3F:
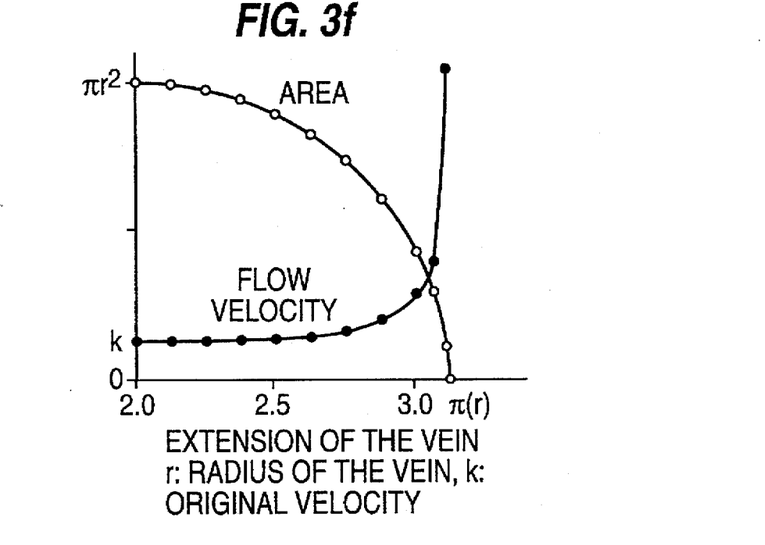
FIG. 3f is a graph showing in vitro test results of the relationship between the area of the vein, when the filtering device is in the vein, in comparison to the blood flow velocity through the vein.

FIG. 3f shows the relationship of the blood flow velocity and extension of the vein at the site the filtering device is placed in the vein. The graph shows that as the blood vessel B is extended from the original circular cross-section to the elliptical cross section shown in FIG. 3d, the area of the blood vessel decreases. Accordingly, the graph illustrates that the blood flow velocity increases inversely to the cross-sectional area decrease of the blood vessel B. Thus, when the active part 1 of the filter device extends the blood vessel B such that the long radius a of the blood vessel B, as shown in FIG. 3d, is three times the original blood vessel radius r, shown in FIG. 3c, the blood flow velocity across the filtering device will be twice the original blood flow velocity.

The results of the in vitro testing of the filtering device shown by the graphs in FIGS. 3e and 3f are taken from the following reports which are hereby incorporated by reference: Frode Laerum, M. D. et al., In Vitro Assessment of the New Adjustable Temporary Venous Spring-Filter, Feb. 26, 1995; and Frode Laerum, M. D., et al., In Vitro Function of the Temporary Venous Spring-Filter Compared to the Filcard Temporary Filter and Greenfield Vena Cava Filter, Feb. 24, 1995.

Figure 4:
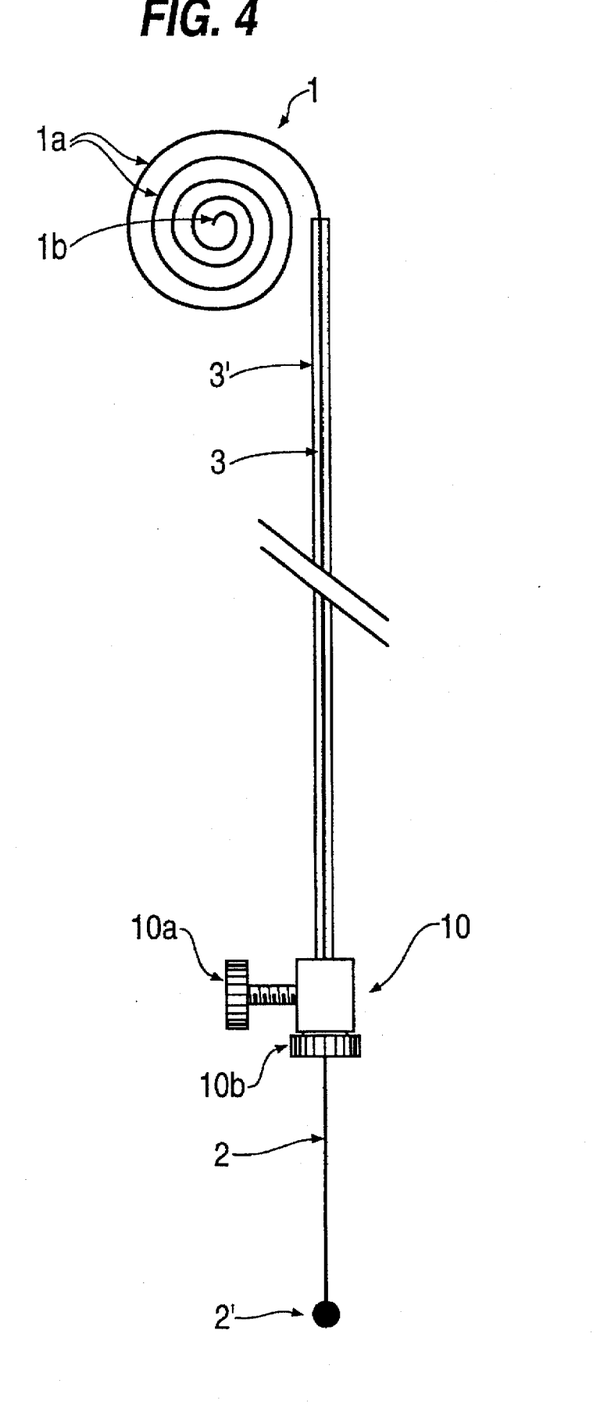
FIG. 4 is a front view of the filtering device of the type shown in FIGS. 1a and 1b provided with a locking mechanism.

As shown in FIG. 4, the filtering device can be provided with a locking mechanism for locking the outer end of catheter 3 to the flexible wire 2. By locking the outer end of catheter 3 to the flexible wire 2, the desired size and number of turns of the active part 1 can be fixed when the catheter tip is positioned within the vein. The locking mechanism 10 for locking the outer end of the catheter 3 to the wire 2 comprises an internal locking mechanism.

The internal locking mechanism can either be a screw 10a, an axial compression screw 10b or both. Both screw devices compress the catheter member against the flexible wire 2 to hold the wire in position. The axial screw device 10b is provided with a compressible concentric rubber membrane to provide the pressing force.

After the locking mechanism locks the end of the catheter to the flexible wire 2, the filter device is further fastened to the skin of the person in which the catheter has been inserted by a fastening device (not shown in figures), either a surgical suture or another commercially available device. This commercially available device may be a catheter introducer. The catheter inducer includes a peripheral opening with a compressible rubber/silicon member with an axial located screw therein. The inducer may be fastened to the skin by a single suture if necessary.

FIG. 4 shows further modifications to the first embodiment shown in FIGS. 1a and 1b. Specifically, the catheter 3 is provided with a strengthened filter section 3' near the end of the catheter that is inserted into the skin. Additionally, the spring loops 1a of the active part 1 terminate with a short flexible end 1b for the purpose of providing a system that readily returns to the configuration of the active part when it extends beyond the end of the catheter.

Figure 5A:
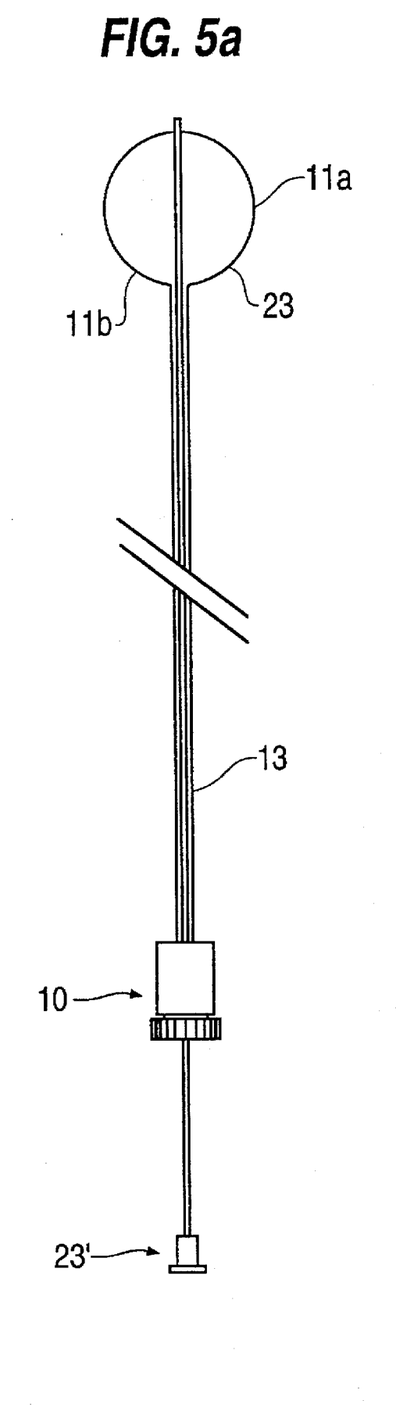
FIG. 5a is a front view of a filtering device according to a third embodiment of the invention in an unfolded (active) state.
Figure 5B:
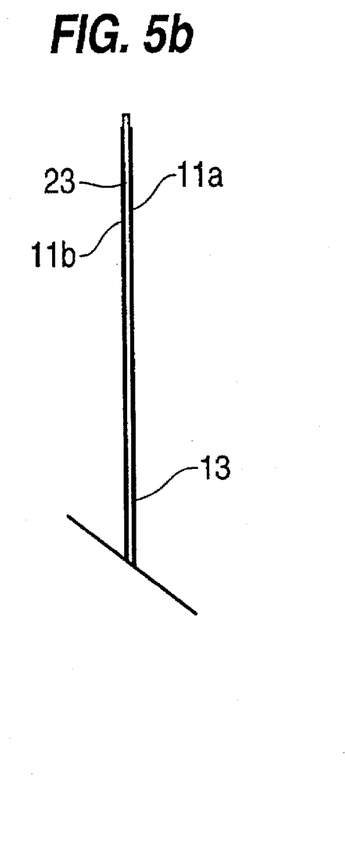
FIG. 5b is a partial front view of the filter device of the type shown in FIG. 5a in a folded (inactive) state.

FIGS. 5a and 5b show a third embodiment of the invention. The figures show a co-axial filtering device. The filtering device is provided with flexible wires 11a and 11b with a shape memory. Although in this embodiment the filter device is shown with a flexible wire, the devices could alternatively be provided with members made out of plastic or another metal, so long as the material possesses the elastic and stability properties required for the function of the device. Each of the flexible wires has a pre-configured memory shape as shown in FIG. 5a. Each end of the wires 11a and 11b is attached to the end of a central catheter 23. The catheter central 23 with end 23' is co-axially arranged within catheter 13. Movement of the central catheter 23 relative to catheter 13 determines how much each of the wires 11a and 11b retain their memory shape configuration. By providing each of the wires with a semi-circular memory shape configuration and arranging the wires opposed to each other, such that when each wire retains its memory shape configuration, the two wires form a circle. The diameter of this circle is thus adjustable by pushing the central catheter 23 along the catheter 13. A locking device 10 is provided for locking the central catheter 23 in position and thus setting the filtering device in an unfolded (active) state.

FIG. 5b shows the end of the filtering device of FIG. 5a in a folded (inactive) state. In this state the central catheter 23 has been pushed through the catheter 13 until the wire members 11a and 11b have been fully extended. This creates the inactive state of the filter device during which the catheter can be placed into the blood vessel.

The circle which is formed from the positioning of the wires 11a and 11b in the active state act as the filter part of the system. Forming this circle, extends the venous wall locally in a slit through which larger formed elements like emboli cannot pass. This arrangement provides a filter device which unfolds in only one plane and with minimal tilt in the axial plane. The filter can easily be positioned in the vein which thus minimizes thrombogenicity.

As with the embodiment disclosed in FIG. 4, the coaxial arrangement as taught by FIGS. 5a and 5b may be secured to the skin of the user by a suture or another commercially available device (introducer).

Figures 6A, 6B:
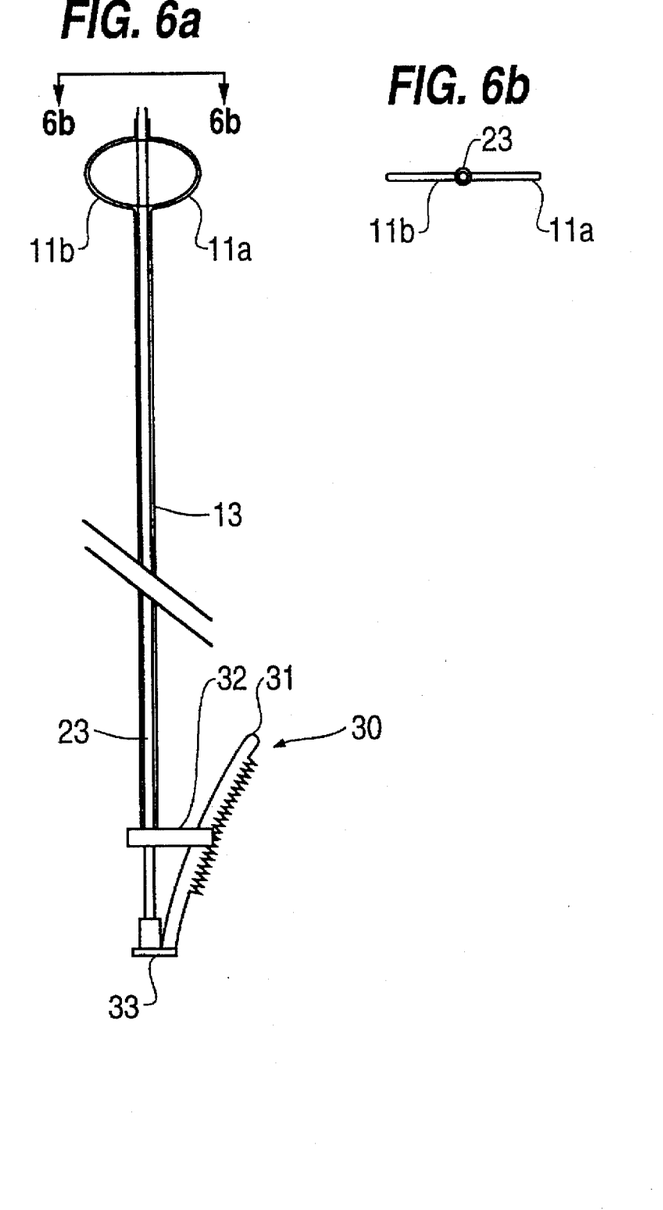
FIG. 6a is a front view of a filter device according to a fourth embodiment of the invention in an unfolded (active) state.
FIG. 6b is a view taken along the line 6b—6b in FIG. 6a, and FIG. 6c is a front view of the filter device according to the fourth embodiment of the invention in a folded (inactive) state.
Figure 6C:
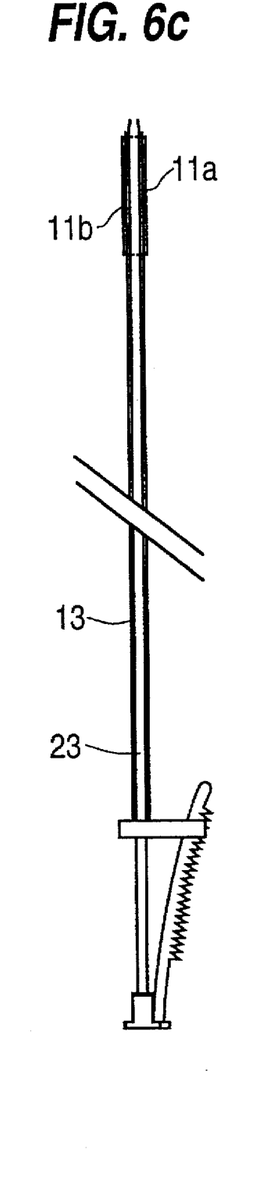

FIGS. 6a–6c show a fourth embodiment of the filter device. The filter shown in FIGS. 6a–6c is similar to the filter device shown in FIGS. 5a and 5b, except that an alternative embodiment of the locking mechanism has been employed. A rachet type locking mechanism 30 is used in the fourth embodiment of the filter device.

As shown in FIG. 6a, the adjustable rachet type locking mechanism 30 is provided with a lever 31 with teeth that engage the lock ring or support 32. The support 32 is securely fixed to the catheter 13. One end of the lever 31 is securely fixed to an end support member 33 which is, in turn, securely fastened to the end of the central catheter 23. Thus, by positioning the teeth in engagement with the lock ring 32 the catheters 13 and 23 are held relative to one another in a locked position.

FIG. 6c shows the fourth embodiment of the filter device in a folded (inactive) state whereby the wire members 11a and 11b are locked in this position by the lever 31 engaging the lock ring 32.

The filtering device, which has been described, is particularly useful to prevent pulmonary embolism caused by venous thrombi and to facilitate new therapeutic methods aiming at local treatment of venous thrombosis by means of fibrinolytic drugs or mechanical thrombo-extractors through stopping blood clots, which, travelling with the blood flow, constitute a potential embolization risk, and giving the venous lumen a slit-like shape, which copies a plicature, at the filter site.

When the embolus risk is considered to be less important, the filter is made to unfold by pulling it backward in the introduction catheter, thus retrieving it from the organism.

Such a filter offers numerous advantages.

The primary advantage is the permanent possibility of retrieval from the organism. Thus, it is possible to retrieve the filtering device when it is no longer needed in order to avoid the long term effects of foreign bodies (local thrombosis, inflammation, penetration and perivenous hematomata).

Unlike conventional vena cava filters, this filter may be used for peripheral veins, i.e. the iliac and femoral veins. As a result, one avoids the potential effects or complications of the filter on the two limbs if only one limb is affected.

In its first embodiment, this filter fits a large number of vein calibers, so that its functioning may be optimized in a more individualized way through a better regulation of the hemodynamics at the filter site.

In its second embodiment, this device is employable for the distension of the dissecting arterial walls or as a vena cava filter catching the emboli.

It will be understood that various modifications in the form of the invention as described herein in its preferred embodiments may be made without departing from the spirit thereof and the scope of the claims which follow.

What is claimed is:

1. A filtering device for preventing embolism and/or the distension of a blood vessel wall, the device comprising:
   a catheter for placement in a blood vessel;
   at least one single flexible wire supported by the catheter including a shape memory portion having an initial flat configuration for engaging the blood vessel wall when said shape memory portion is in an active state; and
   a rectilinear member attached to the shape memory portion;
   wherein the rectilinear portion and the shape memory portion are retractable into said catheter, and form an inactive state when they are retracted inside said catheter, and
   wherein movement of the rectilinear member causes the shape memory portion to return to said initial flat configuration forming said active state so that the at least one single flexible wire will engage the blood vessel wall to cause a maximum deformation of the blood vessel so that the cross-section of said blood vessel becomes essentially elliptic.

2. A filtering device for preventing embolism and/or the distension of a blood vessel wall, the device comprising:
   a catheter for placement in a blood vessel; and
   a single flexible wire supported in the catheter including a spiral shape memory portion for engaging the blood vessel wall and a rectilinear nonshape-memory portion,
   wherein the spiral shape memory portion when supported in the catheter is rectilinear and, when pushed by the nonshape-memory portion out of the catheter, returns to its spiral shape.

3. A device according to claim 2, wherein the nonshape-memory portion extends in the same plane as the shape memory portion.

4. A device according to claim 2, wherein the nonshape-memory portion extends in a plane which is substantially perpendicular to the plane of shape memory portion.

5. A device according to claim 2, wherein coils of the spiral shape memory portion are approximately 3–5 mm apart.

6. A filtering device for preventing embolism and/or the distension of a blood vessel wall, the device comprising:
   a first catheter having an insertion end and a locking end for placement in a blood vessel;
   a central catheter having a first end and a second end disposed co-axially and within the first catheter, the first end being aligned with the insertion end; and
   at least one single flexible wire fixed to the insertion end of the first catheter and to the first end of the central catheter, the wire being provided with a shape memory portion.

7. A device according to claim 6, wherein the shape memory portion is substantially semi-circular.

8. A device according to claim 7, wherein the at least one single flexible wire includes two wires disposed opposite to each other attached to the central catheter.

9. A device according to claim 6, wherein the locking end is provided with a locking mechanism.

10. A device according to claim 9, wherein the locking mechanism comprises a lever pivotally supported on the second end, the lever having teeth that engage a locking ring fixed on the locking end of the first catheter.

11. A device according to claim 8, wherein the two wires form a circle when placed in an active state.

* * * * *